(12) United States Patent
Castellini

(10) Patent No.: US 7,211,220 B2
(45) Date of Patent: May 1, 2007

(54) METHOD FOR CLEANING /DISINFECTING /STERILIZING THE WATER CIRCUITS OF DENTAL UNITS AND A DENTAL UNIT IMPLEMENTING THE METHOD

(75) Inventor: Franco Castellini, Bologna (IT)

(73) Assignee: Castellini S.p.A., Bologna (IT)

( * ) Notice: Subject to any disclaimer, the term of this patent is extended or adjusted under 35 U.S.C. 154(b) by 534 days.

(21) Appl. No.: 10/374,113

(22) Filed: Feb. 25, 2003

(65) Prior Publication Data

US 2003/0175147 A1  Sep. 18, 2003

(30) Foreign Application Priority Data

Mar. 12, 2002 (IT) .......................... BO2002A0124

(51) Int. Cl.
*A61L 2/20* (2006.01)
*A61L 2/24* (2006.01)

(52) U.S. Cl. .......................... 422/28; 422/3; 134/22.12

(58) Field of Classification Search ..................... None
See application file for complete search history.

(56) References Cited

U.S. PATENT DOCUMENTS 4,545,956 A    10/1985  Ciszewski et al.
5,837,204 A *  11/1998  Prevost et al. .............. 422/105
6,019,117 A *   2/2000  Detsch et al. ............ 137/15.05
6,250,920 B1    6/2001  Overmyer

FOREIGN PATENT DOCUMENTS

EP         1029512 A2 *   8/2000
EP         1 161 959      12/2001

* cited by examiner

*Primary Examiner*—E. Leigh McKane
(74) *Attorney, Agent, or Firm*—Fay Sharpe LLP

(57) ABSTRACT

A method for cleaning/disinfecting/sterilizing the water circuits (1) of dental units (100) comprises at least the following steps: introducing a cleaning/disinfecting/sterilizing fluid into the water circuit (1); holding the cleaning/disinfecting/sterilizing fluid in the water circuit (1) for a predetermined length of time; draining the cleaning/disinfecting/ sterilizing fluid out of the circuit (1) through endpieces (3*a*) of supply branches (3); the method further comprising a step of programming/selecting the contact time periods (T) of the steps of introducing and holding the fluid in the water circuit (1), this step preceding the step of introducing the fluid and being effected by selecting from a plurality of contact time periods (T1, T2, T3 . . . Tn) each of which consists at least of a fraction of a time period (Ta) of the step of introducing fluid in the water circuit (1) added to a time period (Tb) of the holding step, according to a desired parameter-level (P1, P2, P3 . . . Pn) of cleaning/disinfection/sterilization and/or of predetermined or predeterminable events on the dental unit (100).

12 Claims, 2 Drawing Sheets

METHOD FOR CLEANING /DISINFECTING /STERILIZING THE WATER CIRCUITS OF DENTAL UNITS AND A DENTAL UNIT IMPLEMENTING THE METHOD

BACKGROUND OF THE INVENTION

The present invention relates to a method for cleaning/disinfecting/sterilizing the water circuits of dental units and to a dental unit implementing the method.

As is by now well within the knowledge of experts in the trade, the water circuits of dental units of the latest generation can be subjected to different types of cleaning/disinfecting/sterilizing cycles depending on requirements: a long or night cycle for aggressive treatment of the water circuit to thoroughly destroy contaminating agents, and a short cycle for quick disinfection of the circuit during the day, for example, between patients or during the lunch break.

In practice, the water circuit, which usually consists of a main fluid supply conduit and a series of branches leading to the handpieces, is supplied with cleaning/disinfecting/sterilizing fluid from an appropriate supply line until the main conduit and the handpiece branches, which are closed by suitable valves, is completely full.

After a predetermined length of time, the cleaning/disinfecting/sterilizing fluid is drained out and the circuit is filled with rinsing or user fluid.

The Applicant, in line with a policy of continual improvement of dental unit hygiene and safety and with a view to extending the capabilities of cleaning/disinfecting/sterilizing cycles, has conducted much research aimed at developing a method, and a dental unit to implement the method, for cleaning/disinfecting/sterilizing the water circuit of the dental unit where the cycle times can be selected from a wide range of programmed times in accordance with the desired degree of aggressiveness on the contaminating agents in the circuit branches and in accordance with the time of day in which the cycle must be carried out.

SUMMARY OF THE INVENTION

The above mentioned aim is accomplished by a method for cleaning/disinfecting/sterilizing the water circuits of dental units comprising the following steps: introducing a cleaning/disinfecting/sterilizing fluid into the water circuit; holding the cleaning/disinfecting/sterilizing fluid in the water circuit for a predetermined length of time; draining the cleaning/disinfecting/sterilizing fluid out of the circuit through endpieces of supply branches; the method further comprising a step of programming/selecting the contact times of the steps of introducing and holding the fluid in the water circuit, this step preceding the step of introducing the fluid and being effected by selecting from a plurality of contact time periods each of which consists at least of a fraction of a time period of the step of introducing the fluid in the water circuit added to a time period of the holding step, according to a desired parameter-level of cleaning/disinfection/sterilization and/or of predetermined or predeterminable events on the dental unit.

BRIEF DESCRIPTION OF THE DRAWINGS

The technical characteristics of the invention, with reference to the above aims, are clearly described in the claims below and its advantages are apparent from the detailed description which follows, with reference to the accompanying drawings which illustrate a preferred embodiment of the invention provided merely by way of example without restricting the scope of the inventive concept, and in which:

DESCRIPTION OF THE PREFERRED EMBODIMENTS

Figure 1:
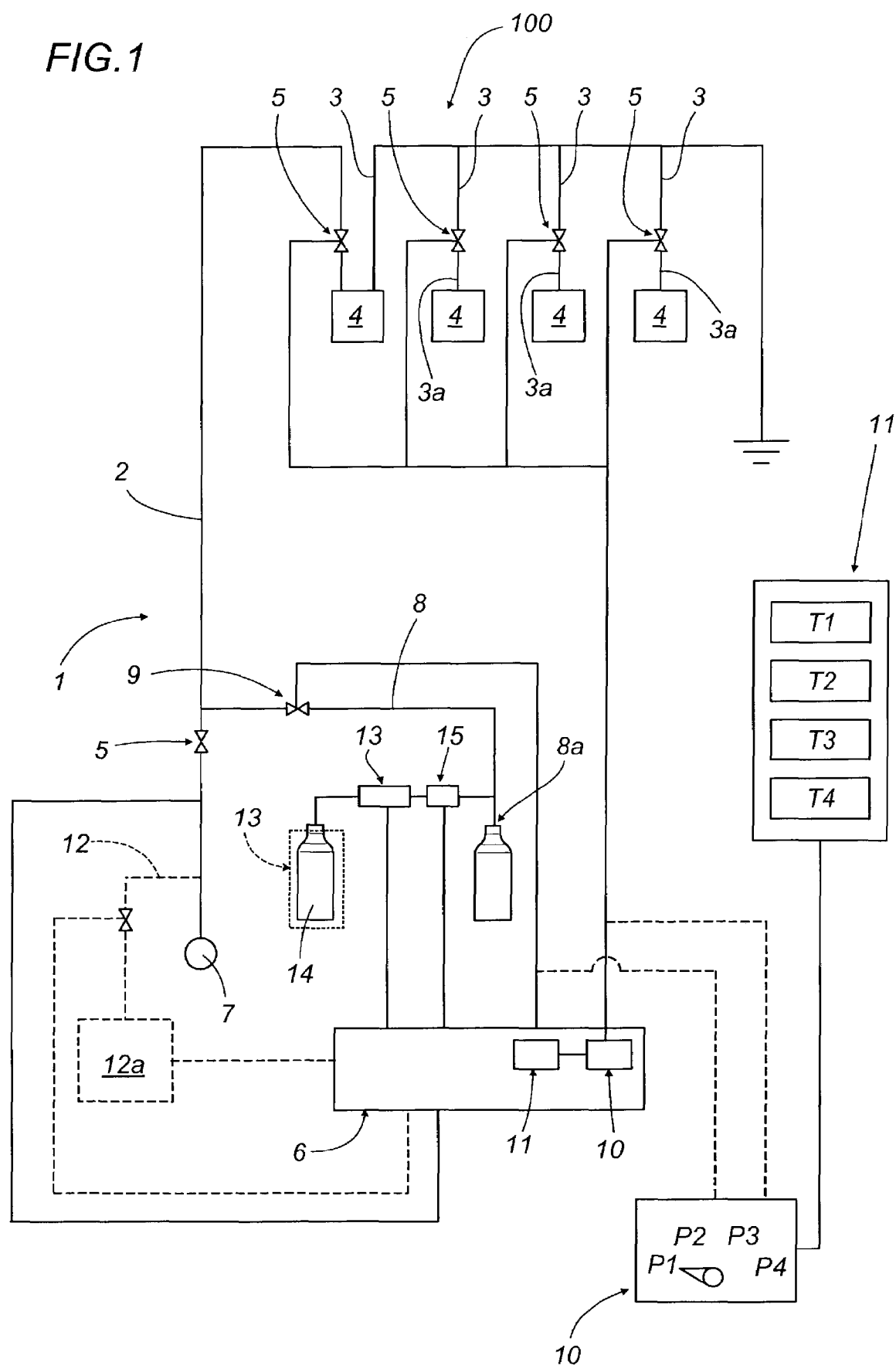
FIG. 1 is a diagram of the water circuit implementing the cleaning/disinfecting/sterilizing method according to the present invention.

With reference to the accompanying drawings, in particular FIG. 1, the method according to the invention is used to clean/disinfect/sterilize the water circuit 1 of a dental unit.

The dental unit, labeled 100, is of the type comprising, at least insofar as is relevant to the present invention, the aforementioned water circuit 1 consisting at least of a main conduit 2 for feeding a user fluid (usually water) from a main supply 7 to a plurality of branches 3 that feed medical instruments 4 (customary handpieces) and equipped with shutoff means 5 (customary valves).

The method according to the invention comprises at least the following steps:

introducing a cleaning/disinfecting/sterilizing fluid into the water circuit 1;

holding the cleaning/disinfecting/sterilizing fluid in the water circuit 1 for a predetermined length of time;

draining the cleaning/disinfecting/sterilizing fluid out of the circuit through endpieces 3a of the supply branches 3, which are usually placed in a suitable container (not illustrated).

The method further comprises a step of programming/selecting the contact time periods T of the steps of introducing and holding the fluid in the water circuit 1, this step preceding the step of introducing the fluid.

This step can be activated by selecting from a plurality of contact time periods, labeled T1, T2, T3 . . . Tn, each of which consists at least of a fraction of a time period Ta of the step of introducing the fluid in the water circuit 1 added to the time period Tb of the holding step, according to a desired parameter-level P1, P2, P3 . . . Pn of cleaning/disinfection/sterilization and/or of predetermined or predeterminable events on the dental unit 100.

The fraction of the time period Ta is defined as Ta-K where K is a constant filling time during which the surfaces of the water circuit 1 cannot be considered as being in contact with the cleaning fluid.

This programming step precedes the step of introducing the fluid and may be performed manually on the dental unit 100 (as described below), or, if the dental unit 100 is fitted with a microprocessor unit 6 for activating and controlling its primary and accessory functions, it may be performed automatically by the microprocessor unit 6 itself before the step of introducing the fluid and according to predetermined or predeterminable events on the dental unit 100.

For example, on the basis of tests and experiments, this programming step consists preferably, but not exclusively, of at least three or four different selections corresponding to the aforementioned cleaning parameter-levels P and/or to the predetermined or predeterminable events on the dental unit 100.

Besides this programming step, the method may comprise, both before the step of introducing the cleaning/disinfecting/sterilizing fluid and after the step of holding the fluid in the water circuit 1, further steps of emptying the user fluid and the cleaning/disinfecting/sterilizing fluid by introducing a gaseous fluid in the water circuit 1 for a predetermined length of time required to completely empty the water circuit 1.

A further addition to the method might be to divide the aforementioned step of introducing the cleaning/disinfecting/sterilizing fluid into two or more sub-steps, each consisting of an inflow of a predetermined quantity or dose of the cleaning/disinfecting/sterilizing fluid alternated with steps of waiting for the next inflow according to the aforementioned contact time periods T selected during the programming step.

More specifically, each of these sub-steps of cleaning/disinfecting/sterilizing fluid inflow is such that the predetermined quantity or dose of the fluid is sufficient to fill and renew the fluid in the water circuit 1, and the waiting time periods between one inflow and the next must be such that an active product is maintained in the circuit at an effective concentration according to the selected contact time periods T.

The method according to the invention comprises a further step of heating the cleaning/disinfecting/sterilizing fluid to a predetermined temperature that is higher than ambient temperature.

This heating step may be carried out during the step of introducing the cleaning/disinfecting/sterilizing fluid, that is to say, inside the water circuit 1, or immediately before the step of introducing the fluid, that is to say, upstream of the water circuit 1.

The dental unit 100 that implements the method described above comprises, in addition to the water circuit 1, an independent sub-circuit 8 for supplying the alternative cleaning/disinfecting/sterilizing fluid to the main conduit 2 and to the aforementioned branches 3, this sub-circuit being equipped with second shutoff means 9 to stop and start the flow of the alternative fluid.

As shown in FIG. 1, the independent sub-circuit 8 has a branch 8a used to supply an alternative user fluid instead of water.

The dental unit 100 comprises programming/selection means 10 acting on the first and second shutoff means 5 and 9 in order to provide a plurality of independent levels P enabling a choice at least of the aforementioned contact time periods T1, T2, T3 . . . Tn of the alternative fluid in the water circuit 1.

Figure 2:
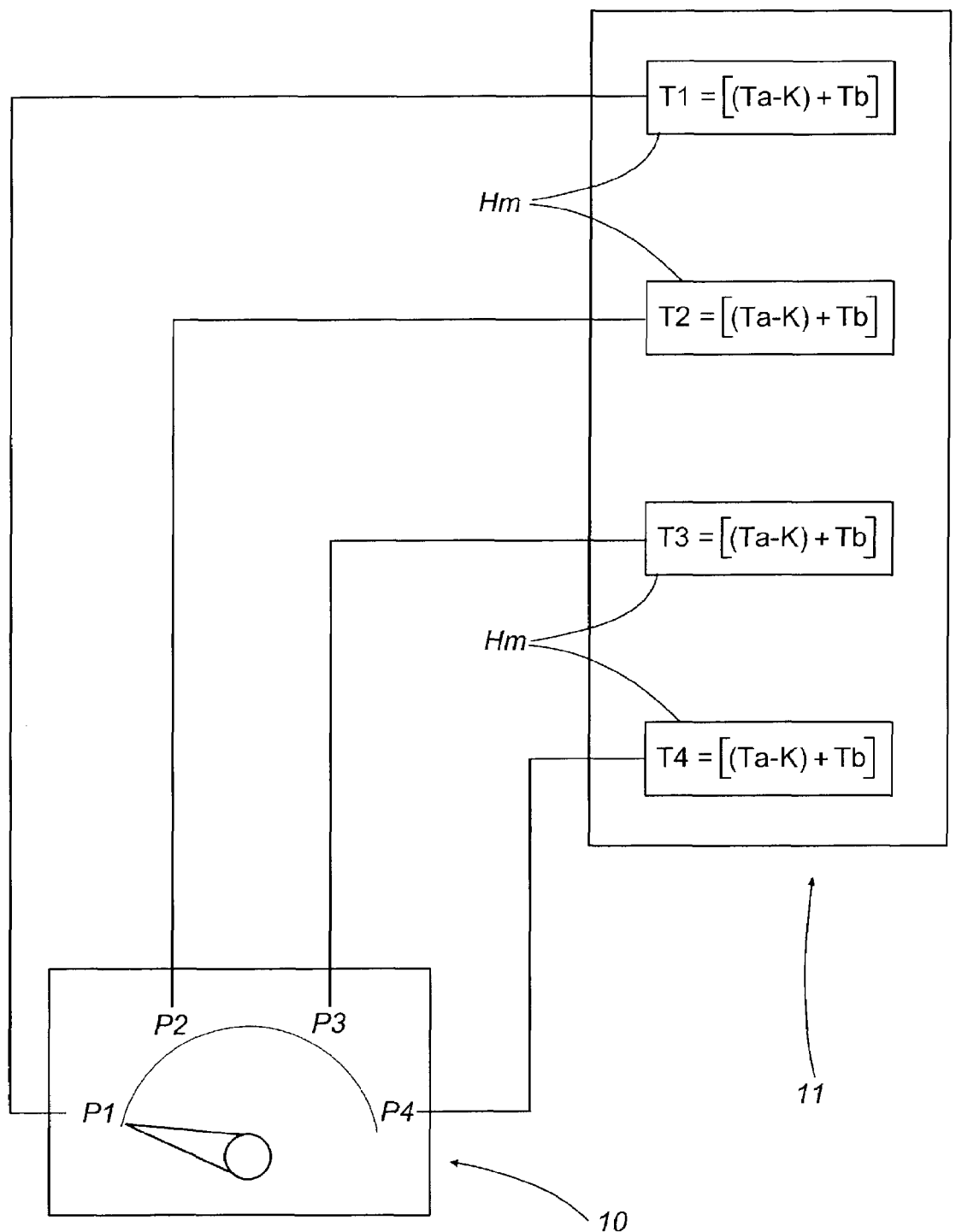
FIG. 2 is a diagram representing a part of the dental unit implementing the method according to the invention.

The programming/selection means 10 may be equipped with timing means 11 (see also FIG. 2) having a plurality of memory banks Hm, each of which stores a value of a contact time period T1, T2, T3 . . . Tn corresponding to a selectable level P for introducing and holding the alternative fluid in the water circuit 1.

As already mentioned, if the dental unit 100 is equipped with a microprocessor unit 6 for activating and controlling its primary and accessory functions, the programming/selection means 10 may be placed under the control of the microprocessor unit 6 which drives the first and second shutoff means 5 and 9 according to the cleaning level P selected using the memory banks Hm and stored in the microprocessor unit 6.

Ideally, on the basis of test results, there are at least four memory banks Hm: a first contact time period T1 for selecting a rapid cleaning cycle P1 corresponding to at least one minute; a second contact time period T2 for selecting a short cleaning cycle P2 corresponding to at least five minutes; a third contact time period T3 for selecting a full cleaning cycle P3 corresponding to at least ten minutes; and a fourth contact time period T4 for selecting a night cleaning cycle P4 of undefined duration.

Therefore, on the basis of the dentist's requirements, the selected level may correspond to a very rapid or a very long cleaning cycle or, in the event of automatic control, may be associated with specific functions of the dental unit: for example, when the position of the dental chair (not illustrated) is reset at the end of a session with one patient, the microprocessor unit 6 may start a rapid cycle P1 or a short cycle P2 to sanitize the water circuit 1 before a session with the next patient starts.

To keep the total time of the cleaning cycles (especially the medium and short cycles) under control to a high degree of accuracy, the main conduit 2 may have leading into it a conduit 12 (represented by a broken line) for supplying a gaseous fluid generated by a compressor 12a or directly by the dental unit 100, in such a way as to enable the water circuit 1 to be emptied of fluid (first the user fluid and then the cleaning fluid) in a rapid and controlled manner in a predetermined length of time.

The numeral 13 denotes means for heating the cleaning/disinfecting/sterilizing fluid to a temperature higher than ambient temperature, as already mentioned above.

In the embodiment illustrated, the heating means 13 may be located either on the independent sub-circuit 8 so that the cleaning/disinfecting/sterilizing fluid is heated while it is flowing in, or, since the independent sub-circuit 8 is supplied by an alternative fluid container 14 that can be removed from the dental unit 100, the heating means 13 may be located on the container 14 itself and may be turned on just before the inflow of fluid into the sub-circuit 8 and into the water circuit 1.

The dental unit 100 may further comprise means 15 for the controlled inflow of cleaning/disinfecting/sterilizing fluid (for example a check valve controlled by the microprocessor unit 6 acting on the independent sub-circuit 8 in order to allow the inflow, in succession, of a plurality of predetermined doses of cleaning/disinfecting/sterilizing fluid.

These elements make it possible to keep the total cycle time within well defined time intervals.

For example, a rapid cycle P1 may consist of the following: a first time period of approximately 60 seconds in which the user fluid is emptied out of the circuit; a contact time period T1 [(Ta−K)+Tb, that is to say, fluid inflow+hold) of 60 to 90 seconds and a further time period 60 to 90 seconds to empty the cleaning fluid out of the circuit. The duration of the rapid cleaning cycle is therefore around 180 to 240 seconds.

The method as described above and the dental unit that implements it thus achieve the aims of the invention thanks to an extremely simple yet effective cleaning/disinfecting/sterilizing structure which keeps the water circuit at a high level of hygiene at all times.

The procedures may be performed very rapidly and do not require onerous and time-consuming programming or preparation, thus enabling the dentist to carry out these important procedures regularly without encroaching on the time required for patient treatment.

The choice of the contact time period depends on the type of treatment that the last patient has undergone or that the next patient will undergo and on the level of hygiene required.

The invention described can be subject to modifications and variations without thereby departing from the scope of the inventive concept. Moreover, all the details of the invention may be substituted by technically equivalent elements.

What is claimed is:

1. A method for cleaning and disinfecting or sterilizing the water circuits (1) of dental units (100), where the water circuit (1) of the dental unit (100) comprises a main conduit (2) for supplying a user fluid from a mains supply (7) to a plurality of branches (3) equipped with shutoff means (5), said plurality of branches (3) for supplying corresponding medical instruments (4) having endpieces (3*a*), the method comprising:

introducing a cleaning and disinfecting or sterilizing fluid into the water circuit (1);
   holding the cleaning and disinfecting or sterilizing fluid in the water circuit (1) for a predetermined length of time; and
   draining the cleaning and disinfecting or sterilizing fluid out of the circuit (1) through endpieces (3*a*) of the supply branches (3);
   wherein the method further comprises a step of programming a contact time period T for the combined steps of introducing and holding the fluid in the water circuit (1) according to a desired parameter level of cleaning and disinfecting or sterilizing andlor of predetermined or predeterminable events on the dental unit (100), this step preceding the step of introducing the fluid and including selecting T from a plurality of contact time periods T1, T2, T3, . . . Tn,
   wherein each contact time period T is defined by the equation $T=[(Ta-K)+Tb]$, and wherein Ta is defined as the time period of the step of introducing the fluid in the water circuit (1),
   K is a constant filling time during which the surfaces of the water circuit (1) cannot be considered to be in contact with the cleaning and disinfecting or sterilizing fluid, and
   Tb is defined as the time period of the holding step.

2. The method according to claim 1, further comprising introducing a gaseous fluid into the water circuit (1) to empty the fluid therefrom after the step of holding the cleaning and disinfecting or sterilizing fluid in the water circuit (1).

3. The method according to claim 1, further comprising introducing a gaseous fluid into the water circuit (1) for a predetermined length of time in order to expel all existing fluid therefrom after the programming step and before the step of introducing the cleaning and disinfecting or sterilizing fluid.

4. The method according to claim 1, further comprising dividing the step of introducing the cleaning and disinfecting or sterilizing fluid into at least two sub-steps, each sub-step comprising of an inflow of a predetermined quantity or dose of cleaning and disinfecting or sterilizing fluid alternated with steps of waiting for the next inflow according to said contact time period T selected during the programming step.

5. The method according to claim 4, wherein the quantity of dose of cleaning and disinfecting or sterilizing fluid flowing in during each of the sub-steps is predetermined and the waiting time periods between one inflow and the next are such that a sufficient and effective concentration of cleaning and disinfecting or sterilizing fluid is maintained in the water circuit for the selected contact time period T.

6. The method according to claim 1, further comprising heating the cleaning and disinfecting or sterilizing fluid to a predetermined temperature higher than ambient temperature.

7. The method according to claim 6, wherein the step of heating the cleaning and disinfecting or sterilizing fluid occurs inside the water circuit (1).

8. The method according to claim 6, wherein the step of heating the cleaning and disinfecting or sterilizing fluid occurs upstream of the water circuit (1).

9. The method according to claim 1, wherein the programming step precedes the step of introducing the cleaning and disinfecting or sterilizing fluid and is performed manually on the dental unit (100).

10. The method according to claim 1, further comprising providing a microprocessor unit (6) to control the functions of the dental unit (100), wherein the programming step is performed automatically by the microprocessor unit (6) before the step of introducing the cleaning and disinfecting or sterilizing fluid and according to predetermined or predeterminable events on the dental unit (100).

11. The method according to claim 1, wherein the programming step comprises at least three different selections corresponding to said parameter level and/or to the predetermined or predeterminable events on the dental unit (100).

12. The method according to claim 1, wherein the programming step comprises at least four different selections corresponding to said parameter level and/or to the predetermined or predeterminable events on the dental unit (100).

* * * * *